United States Patent
Chen et al.

(10) Patent No.: US 9,260,444 B2
(45) Date of Patent: Feb. 16, 2016

(54) CRYSTALLINE FORM OF 2-((1'-N-HEXYLOXY) ETHYL)-2-DIVINYL-PYROPHEOPHORBIDE-A AND METHOD FOR PREPARING THEREOF

(71) Applicant: Zhejiang Hisun Pharmaceutical Co., Ltd., Zhejiang (CN)

(72) Inventors: Zhenliang Chen, Zhejiang (CN); Fei Zheng, Zhejiang (CN); Yumei Wu, Zhejiang (CN); Tianmin Zhu, Zhejiang (CN); Hua Bai, Zhejiang (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 14/377,375

(22) PCT Filed: Feb. 7, 2013

(86) PCT No.: PCT/CN2013/071502
§ 371 (c)(1),
(2) Date: Aug. 7, 2014

(87) PCT Pub. No.: WO2013/117164
PCT Pub. Date: Aug. 15, 2013

(65) Prior Publication Data
US 2015/0099873 A1  Apr. 9, 2015

(30) Foreign Application Priority Data
Feb. 7, 2012  (CN) .......................... 2012 1 0026056

(51) Int. Cl.
*C07D 487/22* (2006.01)
*A61K 41/00* (2006.01)

(52) U.S. Cl.
CPC .......... *C07D 487/22* (2013.01); *A61K 41/0071* (2013.01)

(58) Field of Classification Search
CPC .................................................... C07D 487/22
See application file for complete search history.

(56) References Cited

U.S. PATENT DOCUMENTS 5,198,460 A    3/1993   Pandey et al.
2004/0044198 A1    3/2004   Pandey et al.

FOREIGN PATENT DOCUMENTS

WO    2004005289 A2    1/2004

OTHER PUBLICATIONS

International Search Report for Application No. PCT/CN2013/071502 dated May 16, 2013.
Pandey et al., "Chlorin and Porphyrin Derivatives as Potential Photosensitizers in Photodynamic Therapy", Photochemistry and Photobiology, 1991, 53 (1), 65 to 72.
Pallenberg, "Efficient Synthesis of Pyropheophorbide-a and Its Derivatives", Organic Process Research & Development, 2004, 8, 287 to 290.

*Primary Examiner* — Brian McDowell
(74) *Attorney, Agent, or Firm* — Lerner, David, Littenberg, Krumholz & Mentlik, LLP

(57) ABSTRACT

The present invention provides a crystalline form of HPPH (2-((1'-n-hexyloxy)ethyl)-2-divinyl-pyropheophorbide-a):

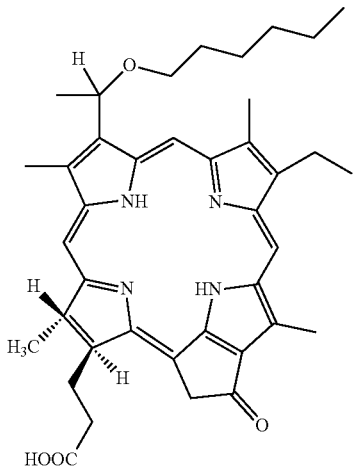

The crystalline form can be characterized by an X-ray powder diffraction (XRD) pattern and differential scanning calorimeter (DSC) pattern. The present invention also provides a method for preparing the crystalline form of HPPH.

11 Claims, 2 Drawing Sheets

CRYSTALLINE FORM OF 2-((1'-N-HEXYLOXY) ETHYL)-2-DIVINYL-PYROPHEOPHORBIDE-A AND METHOD FOR PREPARING THEREOF

CROSS REFERENCE TO RELATED APPLICATIONS

The present application is a national phase entry under 35 U.S.C. §371 of International Application No. PCT/CN2013/071502 filed Feb. 7, 2013, which claims priority to Chinese Application No. 201210026056.5 filed Feb. 7, 2012, the disclosures of which are hereby incorporated herein by reference.

TECHNICAL FIELD

The present invention relates to a crystalline form of HPPH (2-((1'-n-hexyloxy)ethyl)-2-divinyl-pyropheophorbide-a) and to a method for preparing the crystalline form.

BACKGROUND ART 2-((1'-n-hexyloxy)ethyl)-2-divinyl-pyropheophorbide-a (HPPH) is a derivative of pyropheophorbide-n-hexylether, which has been developed by the Roswell Park Cancer Institute. HPPH has strong absorption at 650 nm. In addition, it has a high singlet oxygen quantum yield. As a result, it is considered that the photosensitizer which has the highest efficiency and the brightest future of development. Its structural formula is as follows:

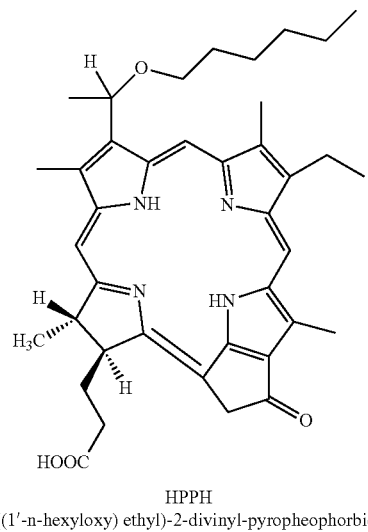

HPPH
2-((1'-n-hexyloxy) ethyl)-2-divinyl-pyropheophorbide-a

In the photodynamic therapy experiment carried out in 5 esophageal cancer patients, at a very low dose, HPPH has exhibited a very good photodynamic therapeutic efficacy. In addition, no photosensitive side effect of skin has been observed clinically.

The research group of Dr. Pandey who was working at the Roswell Park Cancer Institute reported a method for synthesizing HPPH (U.S. Pat. No. 5,198,460; US20040044198A1; *Photochemistry and Photobiology*, 1991, 53 (1), 65 to 72; *Organic Process Research & Development*, 2004, 8, 287 to 290). Up to date, in all of the reports about HPPH, there has been no mention of its crystalline form. However, crystalline form may significantly affect a drug's stability, solubility and bioavailability. In this regard, our research group has studied the preparation method of the crystalline form of HPPH. Moreover, we have obtained a crystalline form of HPPH.

SUMMARY OF INVENTION

In one aspect of the present invention, it provides a crystalline form of HPPH. The crystalline form can be characterized by an X-ray powder diffraction (XRD) pattern and differential scanning calorimeter (DSC) pattern. This crystalline form of HPPH has at least one of the two features set forth below: (1) the characteristic peaks (2θ) of the XRD pattern are: (2θ±0.2) 5.46°, 6.02°, 13.95°, 18.03°, 24.01°, 24.49°; (2) the characteristic peak of the DSC pattern is: a characteristic endothermic peak at 201.2° C.

In one embodiment, the crystalline form of HPPH of the present invention can be characterized by an XRD pattern, wherein the characteristic peaks (2θ) are: (2θ±0.2) 5.46°, 6.02°, 13.95°, 18.03°, 24.01°, 24.49°. In one preferred embodiment, the abovementioned XRD pattern further comprises the characteristic peaks (2θ): (2θ±0.2) 8.66°, 10.92°, 12.04°, 12.44°, 13.31°, 15.0°, 16.90°, 18.94°, 25.03°, 26.28°, 27.21°.

In one exemplary embodiment, the data of 2θ in the XRD pattern of the crystalline form of HPPH of the present invention are shown in the Table 1 below.

TABLE 1

Data of 2θ of the XRD pattern of the crystalline form of HPPH in the present invention

| 2θ (°) | Intensity (%) |
| --- | --- |
| 5.46 | 21.3 |
| 6.02 | 100 |
| 8.66 | 6.8 |
| 10.92 | 4.0 |
| 12.04 | 6.7 |
| 12.44 | 5.9 |
| 13.31 | 5.5 |
| 13.95 | 17.1 |
| 15.0 | 5.4 |
| 16.90 | 9.5 |
| 18.03 | 26.1 |
| 18.94 | 8.5 |
| 24.01 | 30.6 |
| 24.49 | 29.7 |
| 25.03 | 8.5 |
| 26.28 | 2.7 |
| 27.21 | 3.5 |

In one exemplary embodiment, the XRD pattern of the crystalline form of HPPH of the present invention is shown in FIG. 1.

In another embodiment, the crystalline form of HPPH of the present invention can also be characterized by a DSC pattern, wherein the characteristic peak is: a characteristic endothermic peak at 201.2° C. In one exemplary embodiment, the DSC pattern of the crystalline form of HPPH of the present invention is shown in FIG. 2.

In another aspect of the present invention, it provides a method for preparing the crystalline form of HPPH of the present invention. The preparation method comprises the steps set forth below: 1) dissolving an HPPH sample into a polar organic solvent; 2) adding a non-polar solvent to promote the crystallization of HPPH; 3) mixing well, then continuously stirring or sitting undisturbed for 1 to 8 hrs; 4) isolating the obtained crystal. The isolating process comprises the steps of filtering and drying. In this process, the polar solvent is selected from ethyl acetate or acetone, and the non-polar solvent is selected from n-hexane or n-heptane.

In the abovementioned step 1), HPLC purity of the HPPH sample is greater than 90%. The HPPH sample may be dissolved into a polar solvent, acetone or ethyl acetate, but preferably in acetone, wherein the amount of the polar solvent (volume) may be 3 to 15 times the mass of the HPPH sample, but preferably 5 to 10 times, the unit of the ratio of volume to mass is ml/g, the dissolving temperature could be 0° C. to 60° C., but preferably 40° C. to 50° C.

In the abovementioned step 2), the non-polar solvent is selected from n-hexane or n-heptane, but preferably n-heptane. The amount of the non-polar solvent (volume) may be 3 to 15 times the volume of the polar solvent used to dissolve the HPPH sample, but preferably 6 to 10 times.

In the abovementioned step 3), the temperature could be 0° C. to 30° C., but preferably 0° C. to 10° C.

In the abovementioned step 4), the drying temperature could be 0° C. to 60° C., but preferably 30° C. to 50° C.

In yet another aspect of the present invention, it provides a pharmaceutical composition, comprising the abovementioned crystalline form of HPPH of the present invention. In some preferred embodiments of the present invention, the pharmaceutical composition further comprises one or more pharmaceutically acceptable carrier, excipient or diluent and the like. In one preferred embodiment, the pharmaceutical composition of the present invention has been prepared via mixing the crystalline form of HPPH of the present invention and the one or more pharmaceutically acceptable carrier, excipient or diluent.

The pharmaceutical composition of the present invention may have multiple different preparation types. In one preferred embodiment, the preparation type is lyophilized powder.

In yet another aspect of the present invention, it provides an application of the abovementioned crystalline form of HPPH or pharmaceutical composition in preparing medicine. The medicine includes but is not limited to medicine for photodynamic therapy of cancers, medicine for treating skin diseases or medicine for cosmetic purposes.

In regard to its technical effects, the technology disclosed in the present application, as compared with the prior art, has the advantages set forth below. (1) What has been obtained from the preparation process of the present invention is a crystal; whereas in the prior art, there is no crystalline form of HPPH that has been obtained through preparation. It is well-known that crystalline form may affect a drug's stability, solubility and bioavailability. In addition, the preliminary results in our study have shown that the crystalline form of HPPH obtained via the preparation method of the present invention has a desirable stability, which has already been used to prepare a lyophilized powder form of preparation that can be stored at room temperature or in refrigeration, and thus can be used for future studies on photodynamic therapy. (2) In the method disclosed in the prior art, it has used dichloromethane in its preparation, yet according to "The technical guidelines for researches with chemical reagents and residual solvents, (2005 Edition)", dichloromethane is a Category II reagent (with non-hereditary cancer causing property, or may cause other irreversible toxicity (neurotoxicity and teratogenicity), or with other severe but reversible toxicity, should be limited in use), its limited concentration [permitted daily exposure (mg/day)/(1000×Dose (g/day))×100%] is 0.06%. While in the present invention, it utilizes acetone and ethyl acetate. Both acetone and ethyl acetate are Category III reagents (solvent with low toxicity, GMP or other quality that requires limited use). Its limited concentration is 0.5%. (3) The crystal obtained via the method disclosed in the present invention has the features of having a large crystal size and short filtration time, whereas, the samples obtained via the method disclosed in the prior art have a very small particle size and a quite long filtration time.

DESCRIPTION OF EMBODIMENTS

The present invention will be further described in reference to the embodiments. It should be understood that the preparation method disclosed in the embodiments of the present invention is only intended to describe the invention, and not to limit the present invention. The simple modifications of the preparation method of the present invention based on the conception of the present invention are also within the scope claimed in the present invention.

Embodiment 1

Figure 1:
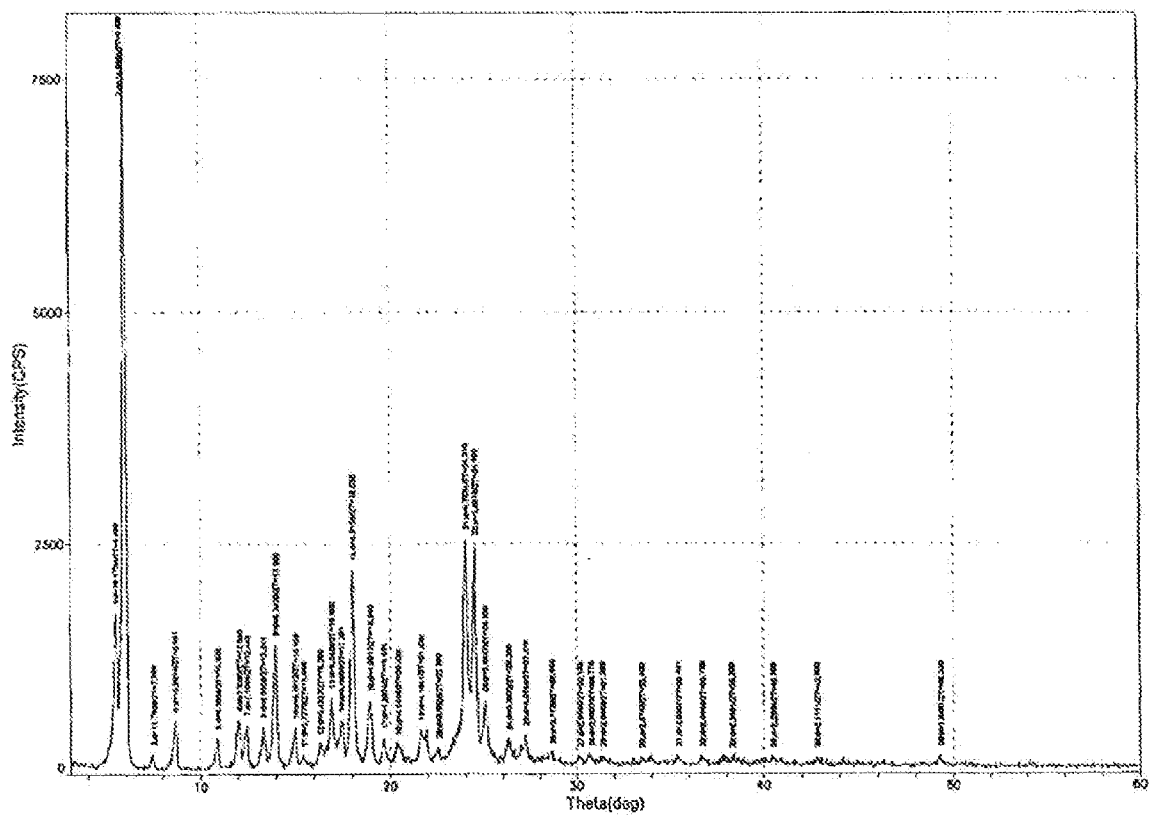
FIG. 1 is the XRD pattern of the crystalline form of HPPH of Embodiment 1 of the present invention.
Figure 2:
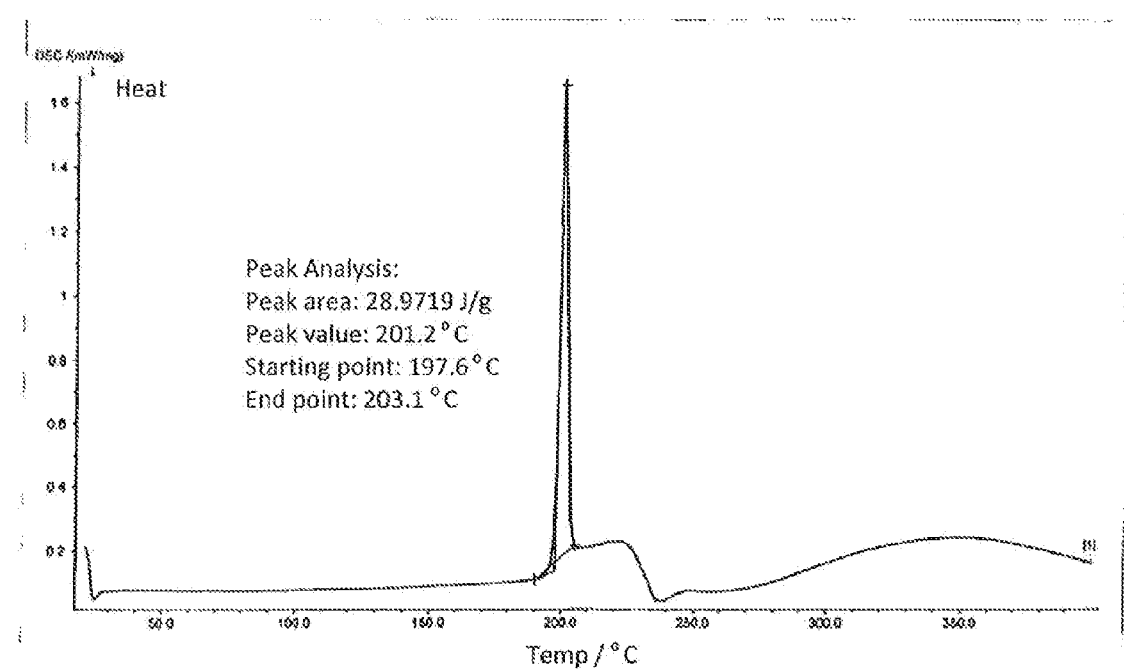
FIG. 2 is the DSC pattern of the crystalline form of HPPH of Embodiment 1 of the present invention.

In a 2 liter eggplant shaped flask, measuring into 17.5 g of HPPH sample (prepared according to the preparation process disclosed in U.S. Pat. No. 5,198,460), adding 100 ml of acetone, stirring, heating with a water bath (40° C. to 45° C.), after the solid is completely dissolved, adding 1050 ml of n-heptane, continuously stirring for 10 minutes, standing undisturbed (at 5° C. to 10° C.) for 6 hrs, filtering, washing filter cake with 100 ml of n-heptane, drying in a vacuum (a vacuum degree greater than 0.9 MPa, at the temperature of 40° C.), so as to obtain 14.2 g of crystalline HPPH product. Next, using Rigaku D/max-2200 (Cu target; voltage: 40 kV; current: 40 mA; Scanning condition: continuous scanning; initial angle: 3°, end angle: 40°, scanning speed: 4/min., Scanning width: 0.01°) to detect XRD pattern of the obtained HPPH product, and using NETZSCH DSC 204 (initial temperature: 20° C.; end temperature: 400° C.; temperature increasing rate: 10.0 K/min) to detect DSC pattern of the obtained HPPH product, and the results are respectively shown in FIG. 1 and FIG. 2.

Embodiment 2

In a 10 liter four necked flask, measuring into 90 g of HPPH sample (prepared according to the preparation process disclosed in U.S. Pat. No. 5,198,460), adding 1.2 liters of ethyl acetate, stirring, heating with a water bath (40° C. to 45° C.), after the solid is completely dissolved, adding 7 liters of n-heptane, continuously stirring for 10 minutes, standing undisturbed (5° C. to 10° C.) for 4 hrs, filtering, washing filter cake with 500 ml of n-heptane, drying in a vacuum (vacuum degree greater than 0.9 MPa, at the temperature of 40° C.), so as to obtain 81.3 g of crystalline HPPH product. With analysis of the XRD pattern (with the same detection condition as described in Embodiment 1), the crystal obtained here is the same as the crystal obtained in Embodiment 1.

Embodiment 3

In a 10 liter eggplant shaped flask, measuring into 51.9 g of HPPH sample (prepared according to the preparation process disclosed in U.S. Pat. No. 5,198,460), adding 400 ml of ethyl acetate, stirring, heating with a water bath (40° C. to 45° C.), after the solid is completely dissolved, adding 3 liters of n-heptane, continuously stirring for 15 minutes, incubating (5° C. to 10° C.) while stirring for 6 hrs, filtering, washing filter cake with 200 ml of n-heptane, drying in a vacuum (vacuum degree greater than 0.9 MPa, at the temperature of 40° C.), so as to obtain 41.4 g of crystalline HPPH product. With analysis of the XRD pattern (with the same detection condition as described in Embodiment 1), the crystal obtained here is the same as the crystal obtained in Embodiment 1.

Embodiment 4

In a 2 liter eggplant shaped flask, measuring into 15.5 g of HPPH sample (prepared according to the preparation process disclosed in U.S. Pat. No. 5,198,460), adding 90 ml of acetone, stirring, heating with a water bath (40° C. to 45° C.), after the solid is completely dissolved, adding 900 ml of n-heptane, continuously stirring for 15 min, standing undisturbed (5° C. to 10° C.) for 5 hrs, filtering, washing filter cake with 80 ml of n-heptane, drying in a vacuum (vacuum degree greater than 0.9 MPa, at the temperature of 40° C.), so as to obtain 12.5 g of crystalline HPPH product. With analysis of the XRD pattern (with the same detection condition as described in Embodiment 1), the crystal obtained here is the same as the crystal obtained in Embodiment 1.

Embodiment 5

1. Long Term Testing

According to the Guidelines to the stability studies of active pharmaceutical ingredient and pharmaceutical preparation (Chinese Pharmacopoeia, 2010 Edition, the Second Part, Appendix XIX C) (Appendix 199 to 200), selecting the HPPH crystal sample prepared in Embodiment 1 (Lot No. S111101), mimicking pack to selling, placing it in an incubator at the temperature of 25° C.±2° C., and the relative humidity of 60%±5%, after 6 months, taking the sample out, and examining it with the key examination items for stability, then comparing the examination results with the results obtained in the 0 month. The results (refer to Table 2) have shown that after the 6 month of long term testing, no examination item has shown significant change, thus the prepared crystalline has a desirable stability.

2. Acceleration Experiment

According to the Guidelines to the stability studies of active pharmaceutical ingredient and pharmaceutical preparation (Chinese Pharmacopoeia, 2010 Edition, the Second Part, Appendix XIX C) (Appendix 199 to 200), selecting the HPPH crystal sample prepared in Embodiment 1 (Lot No. S111101), mimicking pack to selling, placing in an incubator at the temperature of 40° C.±2° C., and the relative humidity of 75%±5%, after 6 months, taking the sample out, and examining it with the key examination items for stability, then comparing the examination results with the results obtained in the 0 month. The results of the accelerated stability test (refer to Table 2) have shown that after the 6 month, its content in the 6 month sample is slightly lower, yet still within the acceptable range, thus it has a desirable stability.

TABLE 2

Stability study data of the HPPH crystal

| Experiment | Stability sample preservation time | Stability sample preservation time (month) | Total impurity (%) | Content (based on dry weight, %) |
|---|---|---|---|---|
| Long term stability experiment | Temp: 25° C. ± 2° C., Humidity: 60% ± 5% | 0 | 0.25 | 99.9 |
| | | 6 | 0.26 | 99.8 |
| Accelerated stability experiment | Temp: 40° C. ± 2° C., Humidity: 75% ± 5% | 0 | 0.25 | 99.9 |
| | | 6 | 0.27 | 98.9 |
| Note | Standard content: 98.0% to 102.0% | | | |

The invention claimed is:

1. A method for preparing the crystalline form of 2-((1'-n-hexyloxy) ethyl)-2-divinyl-pyropheophorbide-a (HPPH) characterized by at least one of the features set forth below:
   (1) characteristic peaks (2θ) of X-ray powder diffraction (XRD) pattern being: (2θ±0.2) 5.46°, 6.02°, 13.95°, 18.03°, 24.01°, 24.49°;
   (2) characteristic peak of differential scanning calorimeter (DSC) pattern: a characteristic endothermic peak being at 201.2° C., comprising the four steps set forth below:
   1) dissolving an HPPH sample into a polar organic solvent;
   2) adding a non-polar solvent to promote crystallization of the HPPH;
   3) mixing the mixture, then continuously stirring or sitting undisturbed for 1 to 8 hrs;
   4) isolating the obtained crystal,
   wherein, the polar solvent is selected from ethyl acetate or acetone, the non-polar solvent is selected from n-hexane or n-heptane, and the step of isolating comprises filtering and drying.

2. The method according to claim 1, characterized by the polar solvent being acetone.

3. The method according to claim 1, characterized by the non-polar solvent being n-heptane.

4. The method according to claim 1, characterized by an amount of the polar solvent (volume) being 3 to 15 times of the mass of the HPPH sample, wherein the unit of the ratio of volume to mass is ml/g.

5. The method according to claim 1, characterized by an amount of the non-polar solvent (volume) being 3 to 15 times of the volume of the polar solvent.

6. The method according to claim 1, characterized by the dissolving temperature being 0° C. to 60° C., the temperature in step 3) being 0° C. to 30° C.

7. The method according to claim 1, characterized by the drying temperature being 0° C. to 60° C.

8. The method according to claim 1, characterized by an amount of the polar solvent (volume) being 5 to 10 times of the mass of the HPPH sample, wherein the unit of the ratio of volume to mass is ml/g.

9. The method according to claim 1, characterized by an amount of the non-polar solvent (volume) being 6 to 10 times of the volume of the polar solvent.

10. The method according to claim 1, characterized by the dissolving temperature being 40° C. to 50° C., the temperature in step 3) being 0° C. to 10° C.

11. The method according to claim 1, characterized by the drying temperature being 30° C. to 50° C.

* * * * *